US 11,696,685 B2

(12) United States Patent
Wu et al.

(10) Patent No.: US 11,696,685 B2
(45) Date of Patent: Jul. 11, 2023

(54) METHOD FOR NON-INVASIVE QUANTIFICATION OF ORGAN FAT USING MAGNETIC RESONANCE APPROACH

(71) Applicant: WUXI MARVEL STONE HEALTHCARE CO., LTD., Wuxi (CN)

(72) Inventors: Ziyue Wu, Wuxi (CN); Krishna Nayak, Wuxi (CN); Chao Wang, Wuxi (CN); Xiao Chen, Wuxi (CN)

(73) Assignee: WUXI MARVEL STONE HEALTHCARE CO., LTD., Wuxi (CN)

( * ) Notice: Subject to any disclaimer, the term of this patent is extended or adjusted under 35 U.S.C. 154(b) by 0 days.

(21) Appl. No.: 17/776,238

(22) PCT Filed: Mar. 3, 2020

(86) PCT No.: PCT/CN2020/077596
§ 371 (c)(1),
(2) Date: May 12, 2022

(87) PCT Pub. No.: WO2021/093224
PCT Pub. Date: May 20, 2021

(65) Prior Publication Data
US 2022/0386871 A1    Dec. 8, 2022

(30) Foreign Application Priority Data

Nov. 12, 2019  (CN) .......................... 201911100893.6

(51) Int. Cl.
*A61B 5/00* (2006.01)
*A61B 5/055* (2006.01)
*G01R 33/34* (2006.01)

(52) U.S. Cl.
CPC .............. *A61B 5/004* (2013.01); *A61B 5/055* (2013.01); *G01R 33/34092* (2013.01)

(58) Field of Classification Search
CPC combination set(s) only.
See application file for complete search history.

(56) References Cited

U.S. PATENT DOCUMENTS 4,683,432 A    7/1987  Young
2018/0220949 A1*  8/2018  Prado ................... A61B 5/4872

FOREIGN PATENT DOCUMENTS

CN    101843484 A    9/2010
CN    102330548 A    1/2012
(Continued)

*Primary Examiner* — Joel F Brutus
(74) *Attorney, Agent, or Firm* — Bayramoglu Law Offices LLC

(57) ABSTRACT

A method for non-invasive quantification of organ fat using a magnetic resonance approach includes: constructing a detection system; connecting a detection area; detection system startup; acquiring data; analyzing data; and performing horizontal data analysis. An external computer, a radio frequency (RF) subsystem, and a portable magnet module are used to construct a system for non-invasive quantification of organ fat based on low-field nuclear magnetic resonance (LF-NMR), which causes no damage, and achieves accurate and non-invasive quantification of organ fat. Specific pulse sequences are used to excite nuclear spin in a target region to generate LF-NMR, so as to achieve "one-click" detection, which is used for fast screening of related diseases such as non-alcoholic fatty liver disease (NAFLD). The system has accurate quantification, and is easy to operate without constraints of operator qualifications.

4 Claims, 4 Drawing Sheets

(56) References Cited

FOREIGN PATENT DOCUMENTS

| | | | |
|---|---|---|---|
| CN | 103857331 | A | 6/2014 |
| CN | 110780247 | A | 2/2020 |
| JP | H06311978 | A | 11/1994 |
| JP | 2007312966 | A | 12/2007 |

* cited by examiner

PREP

METHOD FOR NON-INVASIVE QUANTIFICATION OF ORGAN FAT USING MAGNETIC RESONANCE APPROACH

CROSS REFERENCE TO THE RELATED APPLICATIONS

This application is the national phase entry of International Application No. PCT/CN2020/077596, filed on Mar. 3, 2020, which is based upon and claims priority to Chinese Patent Application No. 201911100893.6, filed on Nov. 12, 2019, the entire contents of which are incorporated herein by reference.

TECHNICAL FIELD

The present disclosure relates to the technical field of nuclear magnetic resonance (NMR) medical detection, and in particular, to a method for non-invasive quantification of organ fat using a magnetic resonance approach.

BACKGROUND

About 25% of the global population is suspected of having non-alcoholic fatty liver disease (NAFLD), and many have not been diagnosed due to lack of feasible, realistic, and accurate early detection and monitoring methods. The current gold standard for the diagnosis of NAFLD in the prior art is liver biopsy, which is expensive and invasive, and is not suitable for early detection. Conventional ultrasound imaging is widely used, but it can only provide qualitative information and is highly operator-dependent. In addition, obesity and excess subcutaneous fat are often present in patients with NAFLD, and it is difficult to obtain reliable results by ultrasonography. Conventional magnetic resonance imaging (MRI) is an emerging NAFLD state monitoring technology that has been widely accepted, but is not universally applicable in routine clinical detection due to its high cost.

The present disclosure uses an external computer, a radio frequency (RE) subsystem, and a portable magnet module to construct a system for non-invasive quantification of organ fat based on low-field NMR (LF-NMR). The LF-NMR causes no damage when acting on a human body, and achieves accurate, non-invasive, and safe quantification of organ fat. Specific pulse sequences are used to excite nuclear spins in a target region and receive echo signal generated from the target region. The pulse sequences are subjected to timing control to achieve "one-click" detection, which is used for fast screening of related diseases such as NAFLD, metabolic syndrome, and non-alcoholic steatohepatitis (NASH). The system has a wide range of applications, is lightweight, easy to carry, and cost-effective, has accurate quantification, and is easy to operate without constraints of operator qualifications. A signal from a region of 5-10 cm under the skin can be obtained with sufficient signal-to-noise ratio, such that the signal can be encoded more effectively. Measurement robustness is high. Noise and interference have a small influence on measurement. In particular, a dictionary matching-based method is less prone to errors in the case of low signal-to-noise ratios, while the low signal-to-noise ratios are typical of the applications covered by this patent. Thus, the shortcomings of the prior art are overcome.

SUMMARY

An objective of the present disclosure is to provide a method for non-invasive quantification of organ fat using a magnetic resonance approach, which reasonably solves the problem of high cost, invasiveness, inapplicability to early screening, strong operator dependence, and inability to achieve quantification of organ fat in the prior art.

The present disclosure adopts the following technical solutions:

A method for non-invasive quantification of organ fat using a magnetic resonance approach includes the following steps:

step I, constructing a detection system: constructing a system for non-invasive quantification of organ fat based on LF-NMR using an external computer, an RF subsystem, and a portable magnet module, where the RF subsystem includes a NMR spectrometer, a power amplifier, one or more preamplifiers, a transmit/receive (T/R) switching module, and RF coil matrix or matrices; the NMR spectrometer provides one-way transmit (Tx) and gate control (GATE) signal to the power amplifier, as well as a T/R switching gate (T/R GATE) signal to the T/R switching module; the power amplifier is connected to the T/R switching module after amplifying a transmitted signal, and the T/R switching module is configured to switch the entire RF subsystem between a transmitting state and a receiving state; in the transmitting state, an RF coil or an RF coil array is configured to transmit an RF pulse; in the receiving state, the RF coil or the RF coil array is configured to receive a magnetic resonance signal generated after an organ fat detection target is excited; the NMR spectrometer is connected to an external computer which controls operations of magnetic resonance pulse sequence command, and transmits the received magnetic resonance signal back to the external computer through a data transmission interface. It also consists of a data processing module to analyze and process NMR data, and a display module to display results with diagnostic values;

step II, attaching to a detection region: closely attach the system's probe to a human body surface adjacent to a target organ for non-invasive quantification of organ fat, where the probe includes a magnet and RF coil(s);

step III, system startup: clicking a system start button to run the system for non-invasive quantification of organ fat;

step IV, acquiring data, where (1) the NMR spectrometer transmits a series of specific RF pulses to the target organ through the RF coil matrix or matrices, excites the nuclear spins of the target region, receives echo signal generated from the target region, performs timing control on the transmission and reception. The pulse sequences include at least a Carr-Purcell-Meiboom-Gill sequence with a fixed or random echo spacing and a CPMG sequence with a fixed or random excitation flip angle, (2) in at least one setting, the pulse sequence includes one or more magnetization preparation modules to enhance contrast, and each of the magnetization preparation modules includes, but is not limited to, inversion recovery (IR), saturation recovery (SR), spectrally selective pulses, $T_2$ preparation pulses, diffusion preparation pulses, and velocity-selective saturation (VSS) pulses, (3) the length and echo spacing of the entire echo train can vary based on the actual constraints, the length of the echo train is usually less than three times of the longest $T_2$ in the sample, the data is overwhelmed by noise beyond this time. Besides, the echo spacing can affect the measurement resulting from different diffusion effects. It also needs to be designed not too small to avoid the influence of ringing effects in an RF transceiver subsystem, and typical parameters are: 5 seconds repetition time (TR), 400 µs echo spacing, and 512 echoes, and (4) in a process of acquiring the data, due to the coil inductance, there is a ringing signal of a certain length after the RF pulse is transmitted, the magnitude of the ringing signal is often much larger than the magnitude of the NMR signal in the LF-NMR and shall be eliminated, a straightforward method is to increase the echo spacing to prevent the ringing signal from mixing into the acquisition signal, but the impacts of the diffusion effects on measurement results are also increased. Another more effective method is to use phase cycling, the phase of the ringing signal is only related to the phase of the refocusing pulse in CPMG and the phase of the receiver, while the phase of the actual signal is codetermined by the excitation pulse, the refocusing pulse and the receiver. Therefore, a simplest way is to use two-step phase cycling: a 0 phase excitation pulse, a 90 phase refocusing pulse and a 0 phase receiver, plus a 0 phase excitation pulse, a −90 phase refocusing pulse and a 0 phase receiver to remove or reduce the ringing signal. The same effects can be achieved with other similar phase cycling settings; in addition, in at least one setting, the above phase cycling techniques are configured to eliminate the influence of other noise or interference on the signal;

step V, analyzing the data: processing echo data and calculating tissue parameters by running an internal processor of the NMR spectrometer and programming or running a result analysis software of the external computer, where the tissue parameters include at least proton density fat fraction (PDFF); multiple steps, including a data filtering method and a curve fitting method based on a tissue model, are combined; the curve fitting method based on the tissue model is achieved by performing model-constrained multi-exponential fitting on the obtained echo signal, comparing signal attenuation curves at different echo spacing, or matching a measured signal with a simulated signal generated based on magnetic resonance physics such as the Bloch equation or variants of the Bloch equation through a dictionary matching-based method. The dictionary matching-based method has higher reliability of analysis results in the case of low signal-to-noise ratio, and the low signal-to-noise ratio is typical for the LF-NMR; and step VI, performing horizontal data analysis: combined with relevant information of other patients from other tests, records or imaging studies, performing comprehensive analysis to form the method for non-invasive quantification of organ fat using a magnetic resonance approach.

Further, the portable magnet module may be set as an ergonomic arc surface fitting with the body surface adjacent to the target organ for signal detection. The back of the portable magnet module may be connected to a magnetic yoke. The magnetic field strength at the back may rapidly attenuate. The portable magnet module may be composed of rare earth permanent magnetic materials, may have a small size and light weight, may support hand-held or bracket mounting, and may be easily adjusted to a position suitable for supine, prone, sitting or standing posture of a subject.

Further, One or more target regions within 3-10 cm below the surface of the magnet may be selected by matching RF transmitting frequencies together with coil spatial sensitivities of the RF coil matrix or matrices. Tissues in one or more depths beneath the skin may be selectively excited by transmitting RF pulses matched with resonant frequencies in the depth direction perpendicular to the inner surface of the magnet. The two directions orthogonal to the depth direction may also be selectively excited. One or more receiving coils with limited sensitive regions may be arranged in an array, and each receiving coil may only detect and receive signals in its sensitive region. Combining the two mechanisms, a specific region may be selected in a three-dimensional (3D) space within a human body to acquire the NMR Further, when the collected data is analyzed in step V, the data filtering method may use a variety of characteristic parameters of the tissue to differentiate tissue components. (1) Tissue component differentiation may be performed based on known or estimated $T_1$ relaxation time, and may be affected by contrast preparation, flip angle, and sequence TR. One of the most straightforward methods is to compare images and data with and without inversion pulses or SR preparation pulses. (2) Tissue component differentiation may be performed based on known or estimated $T_2$ relaxation time, and may be achieved by the model-constrained multi-exponential fitting of the obtained echo signal. (3) The tissue components may be differentiated according to known or estimated diffusion constants. A process of differentiating the tissue components may be achieved by comparing the signal attenuation curves at different echo spacing, and the echo spacing may affect diffusion contrast in the signal, thereby realizing separation of different tissues and fat content. In at least one setting, a combination of the above methods may be used to distinguish the tissue components and fat content, and calculate quantitative content data of the organ fat.

Further, when the collected data is analyzed in step V, the dictionary matching-based method may match the measured signal with the simulated signal generated based on the magnetic resonance physics such as the Bloch equation or the variants of the Bloch equation. Matching may be performed by establishing a complete dictionary or using an established dictionary compression technique such as K-singular value decomposition (K-SVD). Tissues with different fat components may have different and unique signal evolution paths under specific pulse sequences. If the signal evolution paths match one of simulated signal paths, that is, the dictionary, a ratio of the tissues and the fat may be determined to be the same as the dictionary.

The present disclosure has the following beneficial technical effects:

The present disclosure provides the method for non-invasive quantification of organ fat using a magnetic resonance approach, which reasonably solves the problem of high cost, invasiveness, inapplicability to early screening, strong operator dependence, and inability to achieve quantification of organ fat in the prior art.

The present disclosure uses the external computer, the RF subsystem, and the portable magnet module to construct the system for non-invasive quantification of organ fat based on LF-NMR, which causes no damage when acting on a human body, and achieves accurate, non-invasive, and safe quantification of organ fat. Specific pulse sequences are used to excite the nuclear spins in the target region and receive echo signal generated from the target region. The pulse sequences are subjected to timing control to achieve "one-click" detection, which is used for fast screening of related diseases such as NAFLD, metabolic syndrome, and NASH. The system has a wide range of applications, is lightweight, easy to carry, and cost-effective, has accurate quantification, and is easy to operate without constraints of operator qualifications. A signal from a region of 5-10 cm under the skin can be obtained with sufficient signal-to-noise ratio, such that the signal can be encoded more effectively. Measurement robustness is high. Noise and interference have a small influence on measurement. In particular, the dictionary matching-based method is less prone to errors in the case of low signal-to-noise ratios, which are typical of the applications covered by this patent. Thus, the shortcomings of the prior art are overcome.

Figure 1:
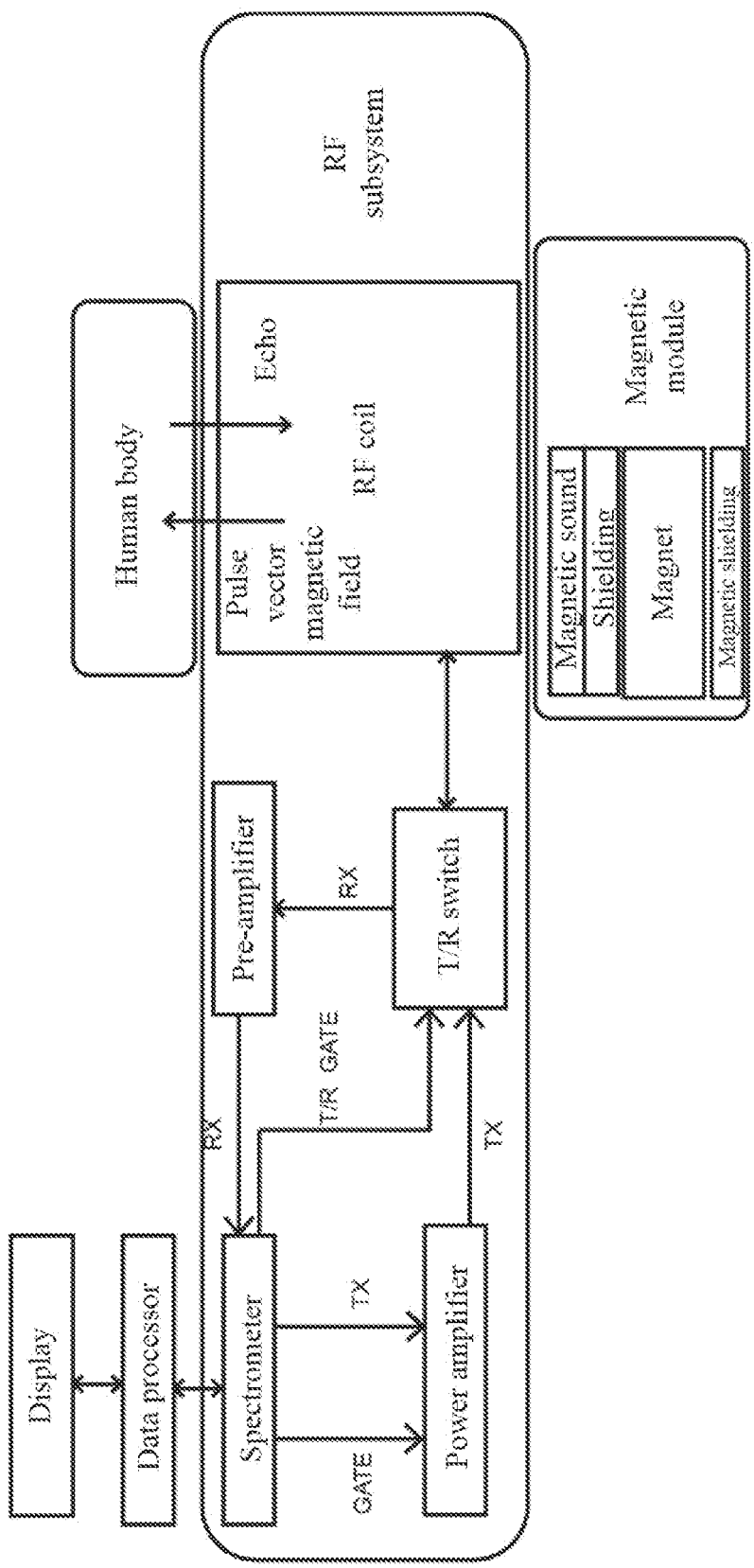
FIG. 1 is a structural diagram of a system architecture used in the present disclosure.
Figure 2:
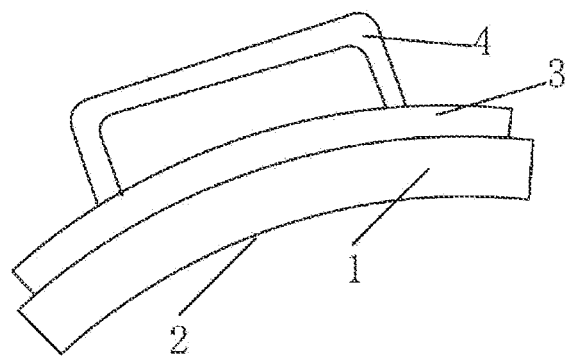
FIG. 2 is a schematic structural diagram of a portable magnet module of the present disclosure.
Figure 3:
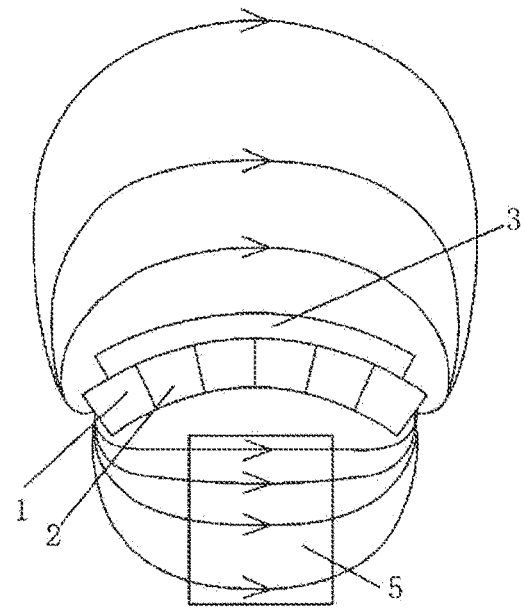
FIG. 3 is a schematic diagram of a magnetic field of the portable magnet module of the present disclosure.
Figure 4:
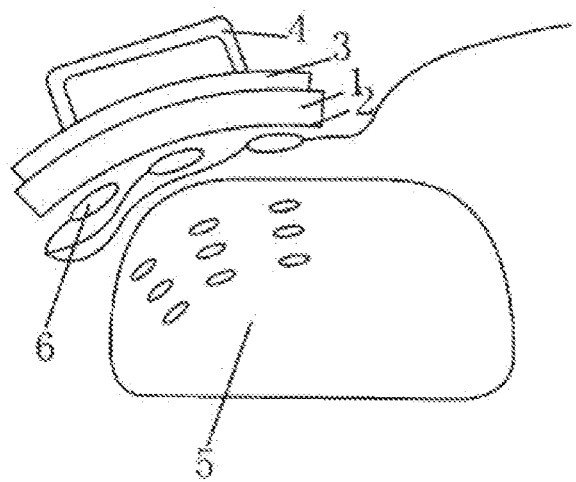
FIG. 4 is a schematic diagram of a detection state of the portable magnet module of the present disclosure.

Reference numerals: 1—portable magnet, 2—ergonomic arc surface, 3—magnetic yoke, 4—handle, 5—region of interest (ROI), and 6—RF coil.

DETAILED DESCRIPTION OF THE EMBODIMENTS

The following description of an embodiment will be more helpful for the public to understand the present disclosure. However, specific embodiment given by the applicant cannot and should not be regarded as limitations on the technical solutions of the present disclosure, and any alterations made to the definitions of components or technical features and/or formal but not substantial change to the overall structure should be regarded as falling within the protection scope defined by the technical solutions of the present disclosure.

Embodiment

As shown in FIG. 1 to FIG. 9, a method for non-invasive quantification of organ fat using a magnetic resonance approach includes the following steps.

Step I, a detection system is constructed: a system for non-invasive quantification of organ fat based on LF-NMR is constructed using an external computer, an RF subsystem, and a portable magnet module. The RF subsystem includes a NMR spectrometer, a power amplifier, one or more pre-amplifiers, a T/R switching module, and RF coil matrix or matrices. The NMR spectrometer provides one-way transmit (Tx) and gate control (GME) signal to the power amplifier, as well as a T/R switching gate (T/R GATE) signal to the T/R switching module. The power amplifier is connected to the T/R switching module after amplifying a transmitted signal. The T/R switching module is configured to switch the entire RF subsystem between a transmitting state and a receiving state. In the transmitting state, an RF coil or an RF coil array is configured to transmit an RF pulse. In the receiving state, the RF coil or the RF coil array is configured to receive a magnetic resonance signal generated after an organ fat detection target is excited. The NMR spectrometer is connected to an external computer which controls operations of magnetic resonance pulse sequence command, and transmits the received magnetic resonance signal back to the external computer through a data transmission interface. It also consists of a data processing module to analyze and process NMR data, and a display module to display results with diagnostic values.

Step II, a detection region is attached: the system's probe is closely attached to a human body surface adjacent to a target organ for non-invasive quantification of organ fat, where the probe includes a magnet and RF coil(s).

Step III, system startup: a system start button is clicked to run the system for non-invasive quantification of organ fat.

Step IV, data is acquired, (1) the NMR spectrometer transmits a series of specific RF pulses to the target organ through the RF coil matrix or matrices, excites the nuclear spins of the target region, receives echo signal generated from the target region, and performs timing control on transmission and reception. The pulse sequences include at least a CPMG sequence with a fixed or random echo spacing and a CPMG sequence with a fixed or random excitation flip angle.

(2) In at least one setting, the pulse sequence includes one or more magnetization preparation modules to enhance contrast, and each of the magnetization preparation modules includes, but is not limited to, IR, SR, spectrally selective pulses, $T_2$ preparation pulses, diffusion preparation pulses, and VSS pulses.

(3) The length and echo spacing of the entire echo train can vary based on the actual constraints. The length of the echo train is usually less than three times of the longest $T_2$ in the sample. The data is overwhelmed by noise beyond this time. Besides, the echo spacing can affect the measurement resulting from different diffusion effects. It also needs to be designed not too small to avoid the influence of ringing effects in an RF transceiver subsystem. Typical parameters are: 5 seconds TR, 400 μs echo spacing, and 512 echoes.

(4) In a process of acquiring the data, due to the coil inductance, there is a ringing signal of a certain length after the RF pulse is transmitted. The magnitude of the ringing signal is often much larger than the magnitude of the NMR signal in the LF-NMR and shall be eliminated. A straightforward method is to increase the echo spacing to prevent the ringing signal from mixing into the acquisition signal, but the impacts of the diffusion effects on measurement results are also increased. Another more effective method is to use phase cycling, the phase of the ringing signal is only related to the phase of the refocusing pulse in CPMG and the phase of the receiver, while the phase of the actual signal is codetermined by the excitation pulse, the refocusing pulse and the receiver. Therefore, a simplest way is to use two-step phase cycling: a 0 phase excitation pulse, a 90 phase refocusing pulse and a 0 phase receiver, plus a 0 phase excitation pulse, a −90 phase refocusing pulse and a 0 phase receiver to remove or reduce the ringing signal. The same effects can be achieved with other similar phase cycling settings. In addition, in at least one setting, the above phase cycling techniques are configured to eliminate the influence of other noise or interference on the signal.

Step V, the data is analyzed: echo data is processed and tissue parameters are calculated by running an internal processor of the NMR spectrometer and programming or running a result analysis software of the external computer. The tissue parameters include at least PDFF. Multiple steps, including a data filtering method and a curve fitting method based on a tissue model, are combined. The curve fitting method based on the tissue model is achieved by performing model-constrained multi-exponential fitting on the obtained echo signal, comparing signal attenuation curves at different echo spacing, or matching a measured signal with a simulated signal generated based on magnetic resonance physics such as the Bloch equation or variants of the Bloch equation through a dictionary matching-based method. The dictionary matching-based method has higher reliability of analysis results in the case of low signal-to-noise ratio, and the low signal-to-noise ratio is typical for the LF-NMR.

Step VI, horizontal data analysis is performed: combined with relevant information of other patients from other tests, records or imaging studies, comprehensive analysis is performed to form the method for non-invasive quantification of organ fat using a magnetic resonance approach.

Further, the portable magnet module is set as an ergonomic arc surface fitting with the body surface adjacent to the target organ for signal detection. The back of the portable magnet module is connected to a magnetic yoke. A magnetic field strength at the back rapidly attenuates. The portable magnet module is composed of rare earth permanent magnetic materials, has a small size and light weight, supports hand-held or bracket mounting, and is easily adjusted to a position suitable for supine, prone, sitting or standing posture of a subject.

Further, one or more target regions within 3-10 cm below the surface of the magnet are selected by matching RF transmitting frequencies together with coil spatial sensitivities of the RF coil matrix or matrices. Tissues in one or more depths beneath the skin are selectively excited by transmitting RF pulses matched with resonant frequencies in the depth direction perpendicular to the inner surface of the magnet. The two directions orthogonal to the depth direction are also selectively excited. One or more receiving coils with limited sensitive regions are arranged in an array, and each receiving coil only detects and receives signals in its sensitive region. Combining the two mechanisms, a specific region is selected in a 3D space within a human body to acquire the NMR signal.

Further, when the collected data is analyzed in step V, the data filtering method uses a variety of characteristic parameters of the tissue to differentiate tissue components, (1) Tissue component differentiation is performed according to known or estimated $T_1$ relaxation time, and is affected by contrast preparation, flip angle, and sequence TR, and one of the most straightforward methods is to compare images and data with and without inversion pulses or SR preparation pulses. (2) Tissue component differentiation is performed based on known or estimated $T_2$ relaxation time, and is achieved by the model-constrained multi-exponential fitting of the obtained echo signal. (3) The tissue components are differentiated according to known or estimated diffusion constants. A process of differentiating the tissue components is achieved by comparing the signal attenuation curves at different echo spacing, and the echo spacing affects diffusion contrast in the signal, thereby realizing separation of different tissues and fat content. In at least one setting, a combination of the above methods is used to distinguish the tissue components and fat content, and calculate quantitative content data of the organ fat.

Further, when the collected data is analyzed in step V, the dictionary matching-based method matches the measured signal with the simulated signal generated based on the magnetic resonance physics such as the Bloch equation or the variants of the Bloch equation. Matching is performed by establishing a complete dictionary or using an established dictionary compression technique such as K-SVD. Tissues with different fat components have different and unique signal evolution paths under specific pulse sequences. If the signal evolution paths match one of simulated signal paths, that is, the dictionary, a ratio of the tissues and the fat is determined to be the same as the dictionary.

Figure 5:
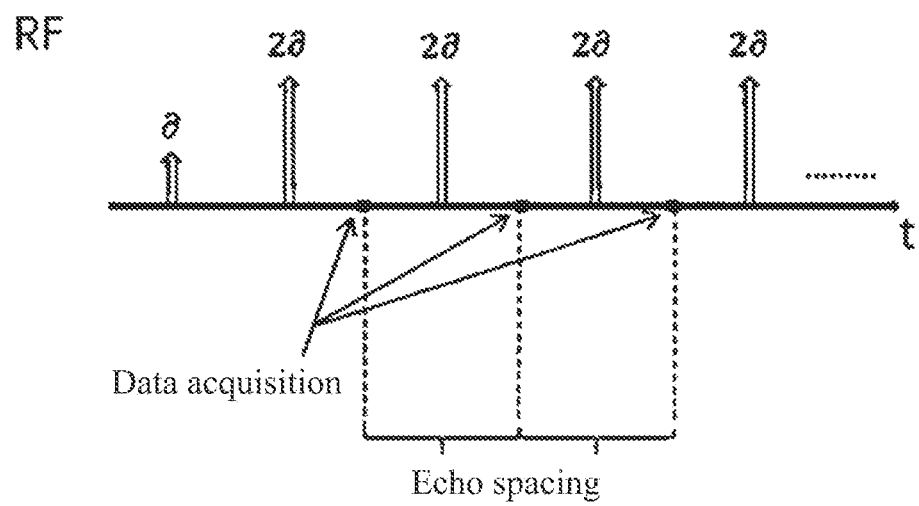
FIG. 5 shows a CPMG pulse sequence of the present disclosure.

Further, in the acquisition of data 2 in step IV, the pulse sequence is set as a CPMG pulse sequence, as shown in FIG. 5. Usually $\alpha=90°$ and $2\alpha=180°$. The echo spacing can be designed to be as short as possible.

Figure 6:
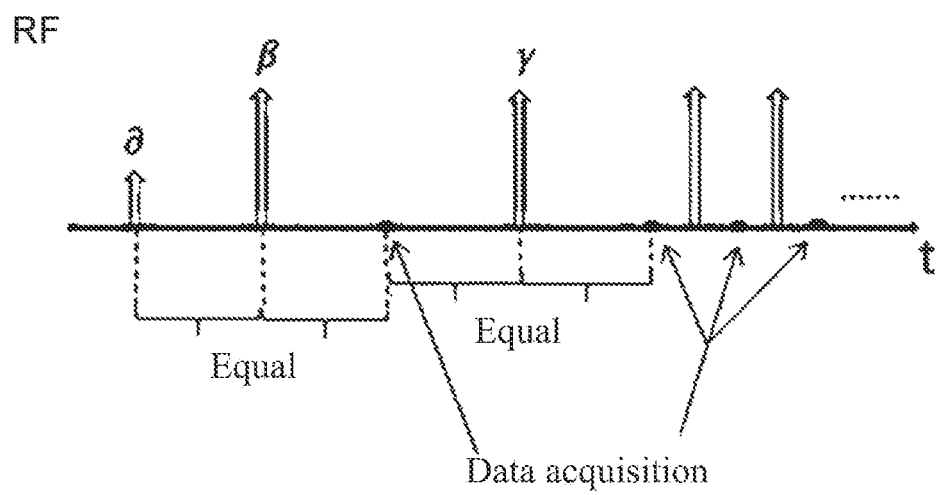
FIG. 6 shows a CPMG with random flip angles and echo spacing of the present disclosure.

In at least one embodiment, a CPMG sequence with a random echo spacing and an excitation flip angle can be used, as shown in FIG. 6.

Figure 7:
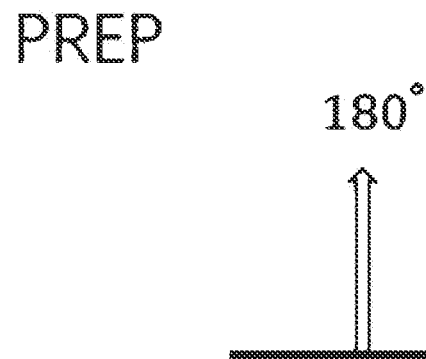
FIG. 7 is an optional IR pulse contrast preparation module diagram of the present disclosure.
Figure 8:
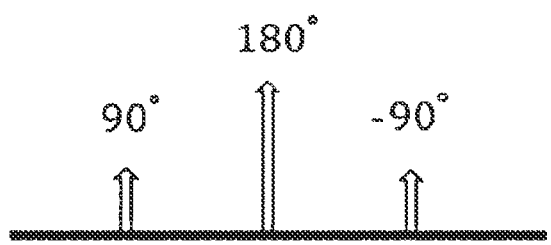
FIG. 8 is an optional $T_2$ preparation pulse contrast preparation module diagram of the present disclosure.

In at least one embodiment, the acquisition sequence will be preceded by one or more magnetization preparation modules to enhance contrast, as shown in FIG. 7 to FIG. 8. Possible magnetization preparation modules include, but are not limited to: IR (FIG. 7), SR, spectrally selective pulses, $T_2$ preparation pulses (FIG. 5), diffusion preparation pulses, and VSS pulses.

Further, in the analysis of the data in step V, in at least one embodiment, tissue components will be differentiated based on known or estimated $T_1$ relaxation time. This will be affected by contrast preparation, the flip angle and sequence TR. One of the most straightforward methods is to compare images with and without inversion or SR preparation pulses.

In at least one embodiment, tissue components will be differentiated based on known or estimated $T_2$ relaxation times. This will be achieved by the model-constrained multi-exponential fitting of the obtained echo signal.

In at least one embodiment, tissue components are differentiated according to known or estimated diffusion constants. This will be achieved by comparing the signal attenuation curves at different echo spacing. The echo spacing affects diffusion contrast in the signal, thereby realizing separation of different tissues and fat content.

In at least one embodiment, a combination of the above methods can be used to distinguish the tissue components and fat content.

Figure 9:
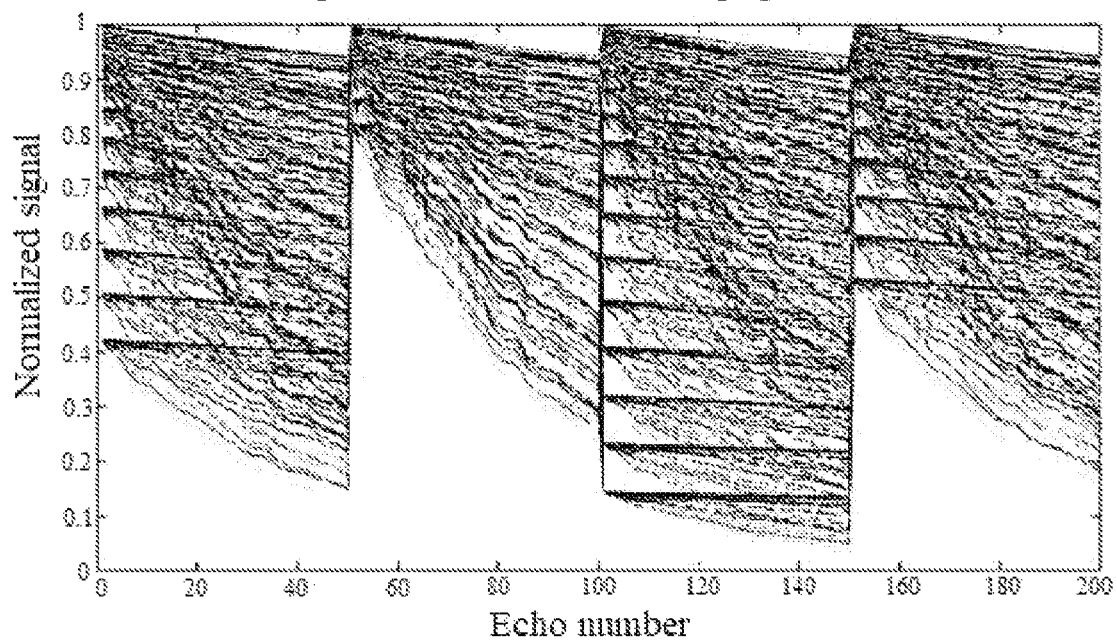
FIG. 9 is a tissue component differentiation diagram based on dictionary matching between measured signals and simulated signals of the present disclosure.

In at least one embodiment, the measured signal can be matched with the simulated signal generated based on the magnetic resonance physics (such as the Bloch equation or the variants of the Bloch equation). Matching can be performed by establishing a complete dictionary or using an established dictionary compression technique (such as K-SVD). FIG. 9 Using the sequences in FIG. 6 to obtain signals, tissues with different fat components have different and unique signal evolution paths (as shown in FIG. 9). If the signal evolution match one of simulated signal paths (the dictionary), a ratio of the tissues and the fat can be determined. The implementation of the method for non-invasive quantification of organ fat using a magnetic resonance approach is completed.

As a matter of course, the present disclosure may further include other various embodiments. A person skilled in the art can make various corresponding modifications and variations according to the present disclosure without departing from the spirit and essence of the present disclosure, and all these corresponding modifications and variations shall fall within the protection scope defined by the appended claims of the present disclosure.

What is claimed is:

1. A method for non-invasive quantification of organ fat using a magnetic resonance approach, comprising the following steps:

step I, constructing a detection system: constructing a system for non-invasive quantification of the organ fat based on a low-field nuclear magnetic resonance using an external computer, a radio frequency subsystem, and a portable magnet module, wherein the radio frequency subsystem comprises a low-field nuclear magnetic resonance spectrometer, a power amplifier, one or more pre-amplifiers, a transmit/receive switching module, and a radio frequency coil; the low-field nuclear magnetic resonance spectrometer provides one-way transmit and gate control signal to the power amplifier and a transmit/receive switching gate signal to the transmit/receive switching module; the power amplifier is connected to the transmit/receive switching module after amplifying a transmitted signal, and the transmit/receive switching module is configured to switch the radio frequency subsystem between a transmitting state and a receiving state; in the transmitting state, the radio frequency coil is configured to transmit radio frequency pulses; in the receiving state, the radio frequency coil is configured to receive a echo signal generated after an organ fat detection target region is excited; the low-field nuclear magnetic resonance spectrometer is connected to an external computer which controls operations of magnetic resonance pulse sequence command, and transmits the received echo signal back to the external computer through a data transmission interface; and the external computer further comprises a data processing module to analyze and process data from low-field nuclear magnetic resonance, and a display module to display results with diagnostic values;

step II, attaching to a detection region: closely attach a probe to a human body surface adjacent to the organ fat detection target region for non-invasive quantification of organ fat, wherein the probe comprises a magnet and the radio frequency coil;

step III, system startup: clicking a system start button to run the system for the non-invasive quantification of the organ fat;

step IV, acquiring data, wherein (1) the low-field nuclear magnetic resonance spectrometer transmit the radio frequency pulses to the organ fat detection target region through the radio frequency coil, excites the nuclear spins of the organ fat detection target region, receives echo signal generated from the organ fat detection target region, and performs timing control on transmission and reception, and the pulse sequences comprise at least a Carr-Purcell-Meiboom-Gill sequence with a fixed or random echo spacing and a Carr-Purcell-Meiboom-Gill sequence with a fixed or random excitation flip angle, (2) in at least one setting of the RF coil, the pulse sequence comprises one or more magnetization preparation modules to enhance contrast, and each of the one or more magnetization preparation modules comprises inversion recovery, saturation recovery, spectrally selective pulses, $T_2$ preparation pulses, diffusion preparation pulses, and velocity-selective saturation pulses, and (3) using two-step phase cycling with a 0 phase excitation pulse, a 90 phase refocusing pulse and a 0 phase receiver, plus a 0 phase excitation pulse, a −90 phase refocusing pulse and a 0 phase receiver to remove or reduce ringing signal from the echo signal;

step V, analyzing the data: processing echo data and calculating tissue parameters by running an internal processor of the low-field nuclear magnetic resonance spectrometer and programming or running a result analysis software of the external computer, wherein the tissue parameters comprise at least proton density fat fraction; performing both a data filtering method and a curve fitting method based on a tissue model; the curve fitting method based on the tissue model is achieved by performing a model-constrained multi-exponential fitting on the echo signal, comparing signal attenuation curves at different echo spacing, or matching a measured signal with a simulated signal generated; and step VI, performing horizontal data analysis: combined with information of other patients from other tests, records or imaging studies, performing analysis to form the method for the non-invasive quantification of the organ fat based on the magnetic resonance approach.

2. The method for the non-invasive quantification of the organ fat based on the magnetic resonance approach according to claim 1, wherein the portable magnet module is set as an ergonomic arc surface fitting with the body surface adjacent to the organ fat detection target region for signal detection; the back of the portable magnet module is connected to a magnetic yoke; the magnetic field strength at the back attenuates; and the portable magnet module is composed of rare earth permanent magnetic materials, supports hand-held or bracket mounting, and can be adjusted to a position suitable for supine, prone, sitting or standing posture of a subject.

3. The method for the non-invasive quantification of the organ fat based on the magnetic resonance approach according to claim 1, wherein the organ fat detection target region within 3-10 cm below the surface of the magnet is selected by matching radio frequency transmitting frequencies together with coil spatial sensitivities of the radio frequency coil; tissues in one or more depths beneath the skin are selectively excited by transmitting radio frequency pulses matched with resonant frequencies in the depth direction perpendicular to the inner surface of the magnet; two directions orthogonal to the depth direction are also selectively excited; a specific region is selected in a three-dimensional space within a human body to acquire the echo signal.

4. The method for the non-invasive quantification of the organ fat based on the magnetic resonance approach according to claim 1, wherein when the collected data is analyzed in step V, the data filtering method differentiates a first tissue component from a second tissue component based on known characteristics of the first tissue component and the second tissue component, (1) tissue component differentiation is performed based on known or estimated $T_1$ relaxation time comparing images and data with and without inversion pulses or saturation recovery preparation pulses; (2) tissue component differentiation is performed based on known or estimated $T_2$ relaxation time and is achieved by the model-constrained multi-exponential fitting of the echo signal; (3) the first tissue component and the second tissue component are differentiated according to known or estimated diffusion constants; a process of differentiating the first tissue component and the second tissue component is achieved by comparing the signal attenuation curves at different echo spacing, and the echo spacing affects diffusion contrast in the echo signal, thereby realizing separation of different tissues and fat content.

* * * * *